(12) United States Patent
Facer

(10) Patent No.: US 12,075,189 B2
(45) Date of Patent: Aug. 27, 2024

(54) TWO-WAY CAMERA OPERATION

(71) Applicant: Udo, LLC, Farmington, UT (US)

(72) Inventor: Steven Ryan Facer, Fruit Heights, UT (US)

(73) Assignee: UDO, LLC, Farmington, UT (US)

(*) Notice: Subject to any disclaimer, the term of this patent is extended or adjusted under 35 U.S.C. 154(b) by 48 days.

(21) Appl. No.: 17/734,952

(22) Filed: May 2, 2022

(65) Prior Publication Data

US 2022/0353463 A1 Nov. 3, 2022

Related U.S. Application Data

(60) Provisional application No. 63/183,411, filed on May 3, 2021, provisional application No. 63/183,421, filed
(Continued)

(51) Int. Cl.
*H04N 7/14* (2006.01)
*G06F 16/16* (2019.01)
(Continued)

(52) U.S. Cl.
CPC .......... *H04N 7/147* (2013.01); *G06F 16/168* (2019.01); *G06F 16/24556* (2019.01);
(Continued)

(58) Field of Classification Search
CPC .......... H04N 7/147; H04N 7/144; H04N 7/14; G16H 40/67; G16H 10/60; G16H 15/00;
(Continued)

(56) References Cited

U.S. PATENT DOCUMENTS

2003/0120514 A1 6/2003 Rao et al.
2003/0146982 A1* 8/2003 Tindall ................... H04N 23/88
348/182

(Continued)

OTHER PUBLICATIONS

International Search Report and Written Opinion received for PCT Patent Application No. PCT/US2022/027422, mailed on Sep. 2, 2022, 11 pages.

(Continued)

*Primary Examiner* — Yosef K Laekemariam
(74) *Attorney, Agent, or Firm* — Workman Nydegger

(57) ABSTRACT

A computing system includes a first camera, a second camera, a microphone, and a display. The computing system is configured to independently activate the first camera and/or the second camera. The computing system first receives a user input initiating a two-way camera operation using both the first camera and the second camera. In response to the user input, the computing system activates the first camera and generates a first visualization, displaying a first image generated by the first camera, and activates the second camera and generates a second visualization, displaying a second image generated by the second camera. Both the first visualization and the second visualization are simultaneously displayed on the display of the computing system, while functions of each of the first camera and second camera can be started, stopped paused unpaused or modified individually.

17 Claims, 16 Drawing Sheets

Related U.S. Application Data on May 3, 2021, provisional application No. 63/183,414, filed on May 3, 2021, provisional application No. 63/183,409, filed on May 3, 2021, provisional application No. 63/183,419, filed on May 3, 2021.

(51) Int. Cl.
| | |
|---|---|
| *G06F 16/2455* | (2019.01) |
| *G06F 16/2457* | (2019.01) |
| *G06F 21/62* | (2013.01) |
| *G16H 10/60* | (2018.01) |
| *G16H 15/00* | (2018.01) |
| *G16H 40/67* | (2018.01) |

(52) U.S. Cl.
CPC .... *G06F 16/24573* (2019.01); *G06F 21/6254* (2013.01); *G16H 10/60* (2018.01); *G16H 15/00* (2018.01); *G16H 40/67* (2018.01); *H04N 7/144* (2013.01); *H04N 2007/145* (2013.01)

(58) Field of Classification Search
CPC ......... G06F 16/24573; G06F 16/24556; G06F 16/168; G06F 21/6254; G06F 16/16; G06F 21/62
See application file for complete search history.

(56) References Cited

U.S. PATENT DOCUMENTS

| | | |
|---|---|---|
| 2009/0299977 A1 | 12/2009 | Rosales |
| 2010/0149372 A1 | 6/2010 | Silverstein |
| 2010/0220906 A1 | 9/2010 | Abramoff et al. |
| 2012/0274808 A1 | 11/2012 | Chong et al. |
| 2013/0138670 A1 | 5/2013 | Ludwig et al. |
| 2013/0268555 A1 | 10/2013 | Utsunomiya |
| 2014/0307101 A1* | 10/2014 | Cobb ............... H04N 9/8227 348/169 |
| 2015/0229849 A1 | 8/2015 | Shin |
| 2018/0249047 A1 | 8/2018 | Marlatt |
| 2020/0260049 A1 | 8/2020 | Erna |
| 2020/0265961 A1* | 8/2020 | Celmins ......... H04N 21/42204 |
| 2022/0351814 A1 | 11/2022 | Facer et al. |

OTHER PUBLICATIONS

International Search Report and Written Opinion received for PCT Patent Application No. PCT/US2022/027411, mailed on Aug. 16, 2022, 14 Pages.
International Search Report and Written Opinion received for PCT Patent Application No. PCT/US2022/027411, mailed on Nov. 16, 2023, 11 Pages.
International Search Report and Written Opinion received for PCT Patent Application No. PCT/US2022/027422, mailed on Nov. 16, 2023, 09 Pages.

* cited by examiner

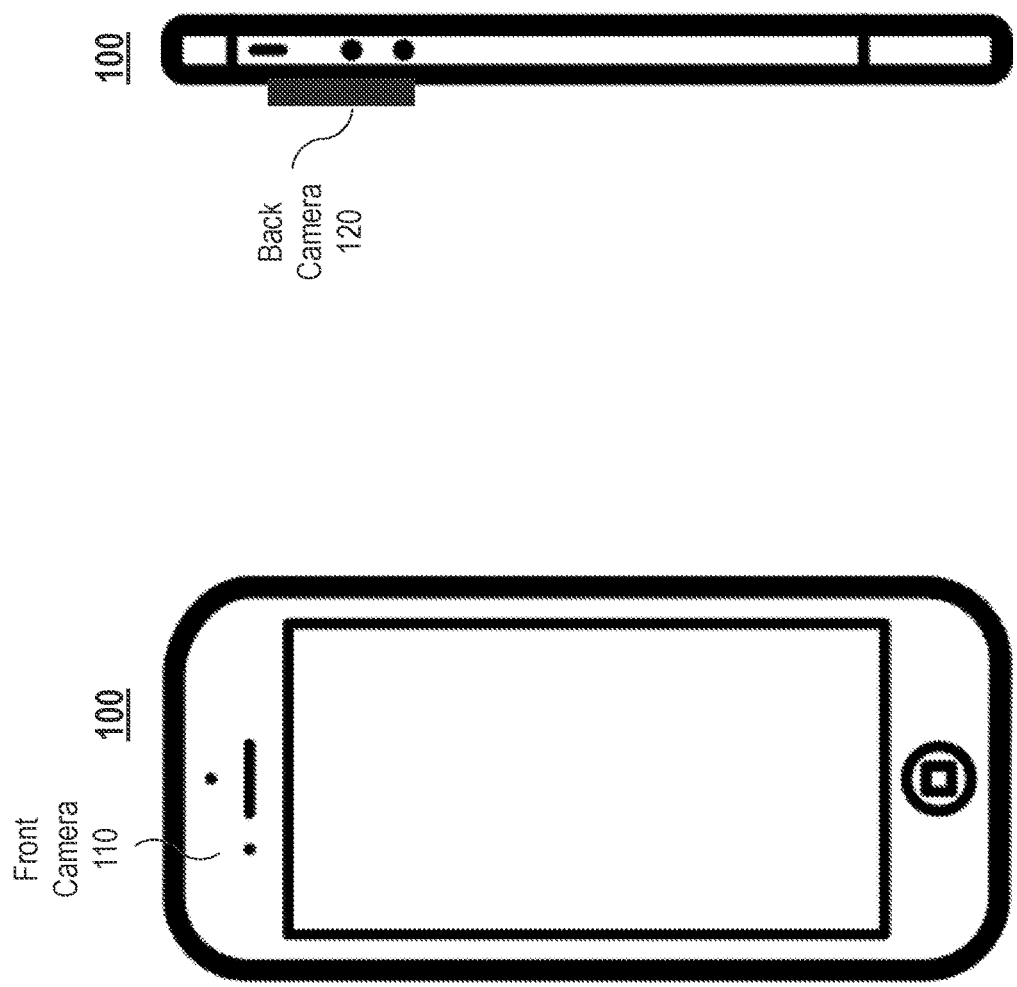

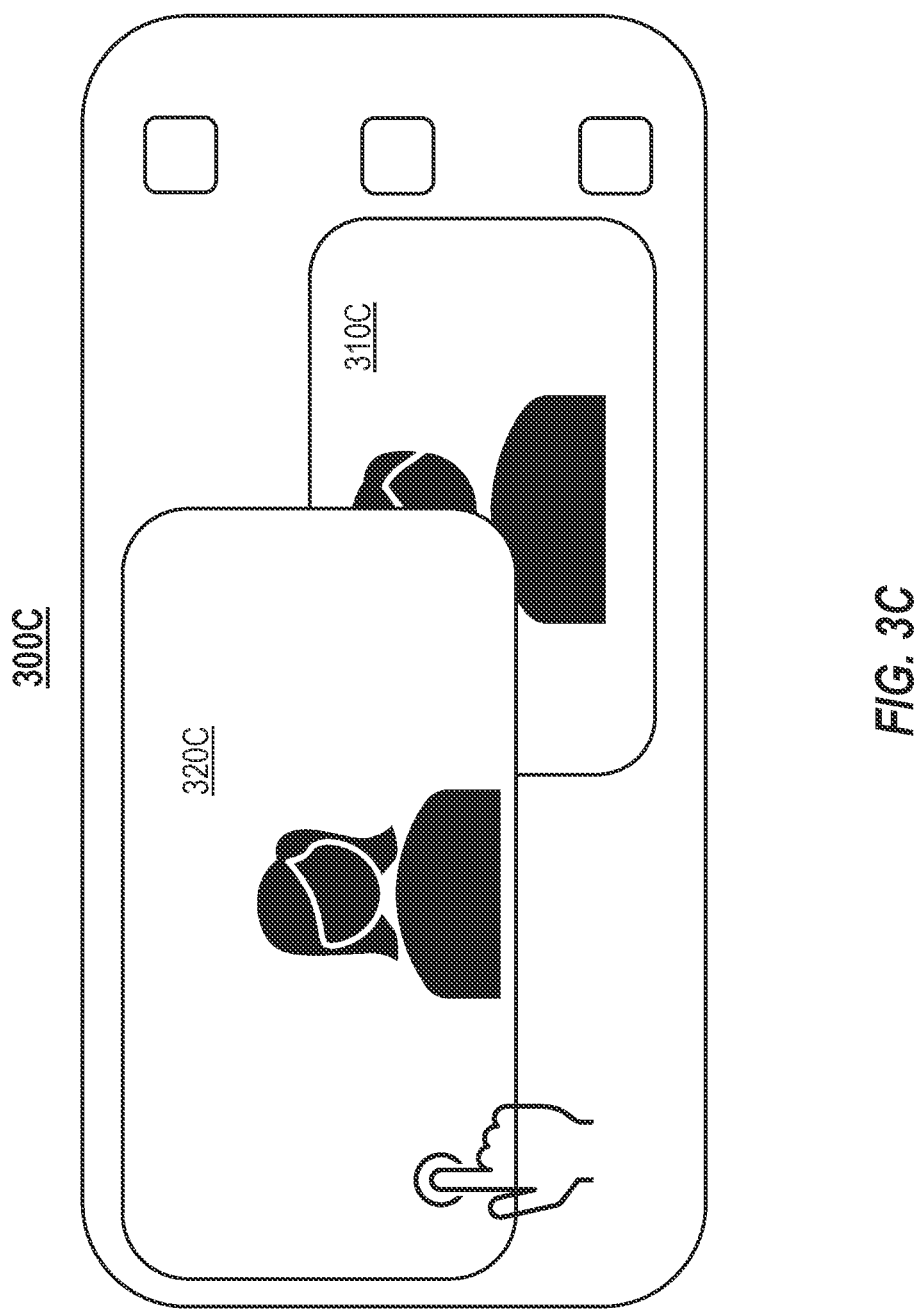

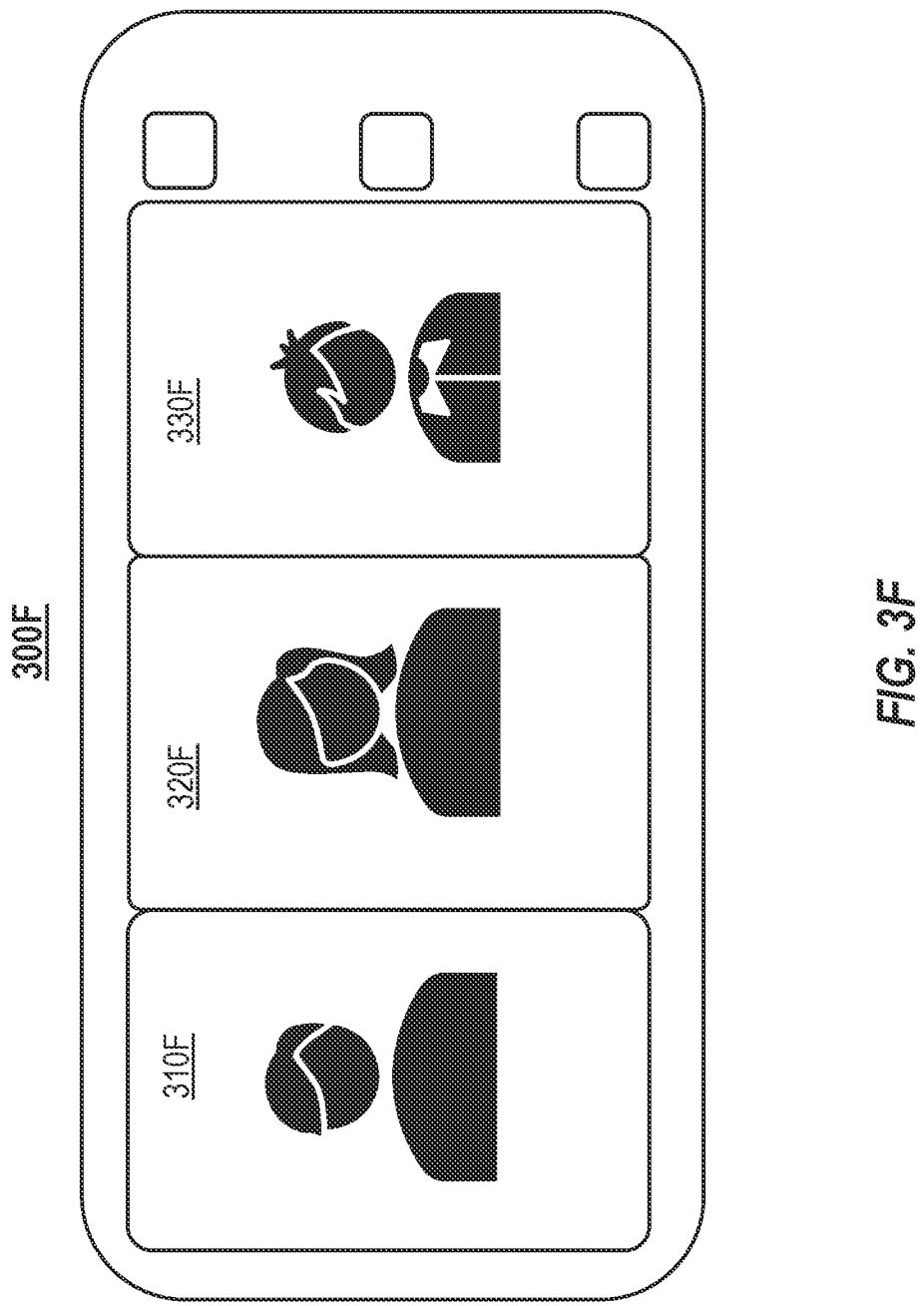

Take a picture of a reference color chart by a camera, a set of standard colors are printed on the reference color chart 710

↓

Compare a set of colors in the picture with a correct set of colors corresponding to a set of standard colors printed on the reference color chart to determine the set of colors in the picture does not matches the correct set of colors 720

↓

Adjust a color balance of the camera, causing the camera to take pictures with the correct set of colors 730

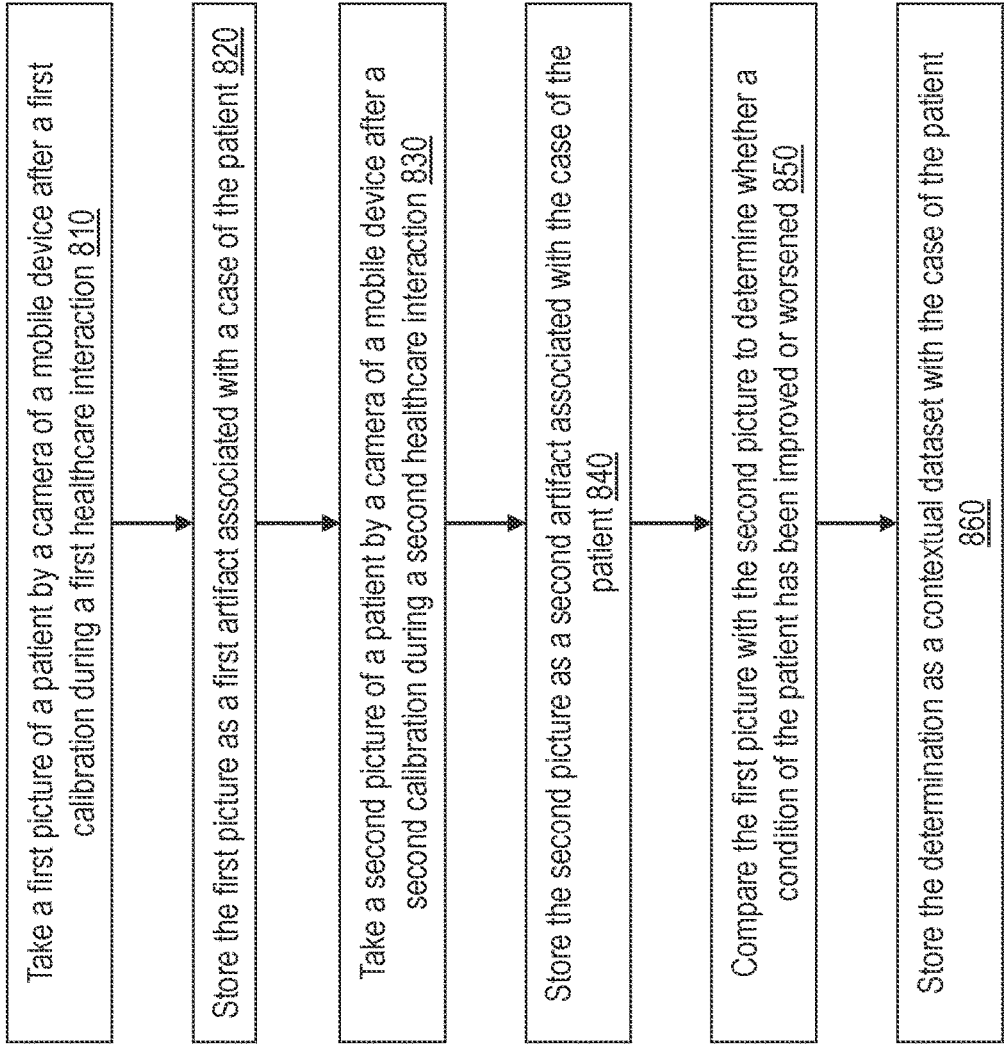

TWO-WAY CAMERA OPERATION

CROSS-REFERENCE TO RELATED APPLICATION

This application claims the benefit of (1) U.S. Provisional Application No. 63/183,409, filed May 3, 2021, entitled "Two-Way Camera Operation", (2) U.S. Provisional Application No. 63/183,411, filed May 3, 2021, entitled "Security and Verification with a Data Sharing Platform", (3) U.S. Provisional Application No. 63/183,414, filed May 3, 2021, entitled "User Invitation for Accessing Healthcare Data", (4) U.S. Provisional Application No. 63/183,419, filed May 3, 2021, entitled "Stitching Related Healthcare Data Together", and (5) U.S. Provisional Application No. 63/183,421, filed May 3, 2021, entitled "Training AI Models for Diagnosing Diseases or Generating Treatment Plans." All of the aforementioned applications are incorporated by reference herein in their entirety.

BACKGROUND

A mobile device is often equipped with two camera lenses on opposite sides of the mobile device. Users are allowed to select one of the two camera lenses to capture images or videos. For example, users may be required to select either the front camera which faces the user or the back camera that faces away from the user when using an image capturing or video recording application.

Many in-person meetings are important meetings. Parties in these meetings may want to record the conversations. When only a mobile device is available, an audio recording may be performed. Alternatively, video recording may be used to record people on one side of the table.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The embodiments described herein are related to a computing system including a first camera, a second camera, a microphone, a display, one or more processors, and one or more computer-readable storage devices having stored thereon executable instructions that, when executed by the one or more processors, configure the computer system to perform various acts independently. The computing system is configured to receive a user input initiating a two-way camera operation using both the first camera and the second camera. In response to the user input, the computing system is configured to activate the first camera and generate a first visualization, displaying a first image generated by the first camera; and configured to activate the second camera and generate a second visualization displaying a second image generated by the second camera. The computing system is further configured to display both the first visualization and the second visualization simultaneously on the display of the computing system. Because activations of the first camera and the second camera are independent, functions of each of the first camera and second camera can be started, stopped, paused, unpaused, or modified individually.

In some embodiments, the computing system is further configured to receive a second user input, indicating starting a video recording. In response to the second user input, the computing system is configured to record a first video generated by the first camera and/or a second video generated by the second camera simultaneously and store the first video and the second video relationally in the one or more computer-readable hardware storage devices. In some embodiments, the computing system is further configured to activate the microphone when the first camera or the second camera is activated and start an audio recording when the first video and the second video are simultaneously recorded. The recorded audio is stored with the first video and the second video relationally in the one or more computer-readable hardware storage devices.

While embodiments and/or examples described herein generally relate to the healthcare industry, the subject matter herein applies and/or relates to other industries including, but not limited to, legal, education, financial, etc. In some embodiments, the computing system is further configured to record a healthcare interaction as a first video dataset, a second video dataset, and an audio dataset. The audio dataset contains a conversation between a healthcare provider and a patient, the first video dataset contains actions of the healthcare provider during the healthcare interaction, and the second video dataset contains actions of the patient during the healthcare interaction. The audio dataset is generated by the microphone, the first video dataset is generated by a first camera, and the second video dataset is generated by the second camera. The first video dataset and the second video dataset are stored as an artifact associated with a case of the patient.

In some embodiments, the computing system is further configured to calibrate a color balance of the first camera or the second camera based on a reference color chart. In some embodiments, calibrating the color balance of the first camera or the second camera includes taking a picture and/or a video of the reference color chart by the first camera or the second camera, and comparing a set of colors in the picture with a correct set of colors corresponding to the reference color chart to determine whether the set of colors in the picture matches the correct set of colors. In response to determining that the set of colors does not match the correct set of colors, the color balance of the first camera or the second camera is adjusted, causing the first camera or the second camera to take pictures and/or videos with the correct set of colors.

The computing system is further configured to take a first picture of the patient by the first camera or the second camera after a first calibration during a first healthcare interaction and store the first picture or video as a first artifact associated with a case of the patient. The computing system is further configured to take a second picture or video of the patient by the first camera or the second camera after a second calibration during a second healthcare interaction and store the second picture or video as a second artifact associated with the case of the patient. The computing system then compares the first picture or video with the second picture or video to determine how a condition of the client has changed (e.g., whether a condition of the patient has been improved or worsened) and stores the determination as a contextual dataset with the case of the patient.

The embodiments described herein are also related to a computer-implemented method for performing a two-way camera operation independently. The method includes receiving a user input, initiating a two-way camera operation using both a first camera and a second camera. The method further includes in response to the user input, activating the first camera and generate a first visualization, displaying a first image generated by the first camera; and activating the second camera and generating a second visualization, displaying a second image generated by the second camera. The method further includes displaying both the first visualization and the second visualization simultaneously on the display of the computing system. Because activations of the first camera and the second camera are independent, functions of each of the first camera and second camera can be started, stopped, paused, unpaused, or modified individually.

The embodiments described herein are also related to computer program product, including one or more computer-readable hardware storage devices having stored thereon computer-executable instructions that are structured such that, when the computer-executable instructions are executed by one or more processors of a computing system, the computer-executable instructions configure the computing system to perform various acts independently. The computing system is configured to receive a user input initiating a two-way camera operation using both a first camera and a second camera coupled to the computing system. In response to receiving the user input, the computing system is configured to activate the first camera and generate a first visualization, displaying a first image generated by the first camera; and configured to activate the second camera and generate a second visualization displaying a second image generated by the second camera. The computing system is further configured to display both the first visualization and the second visualization simultaneously on the display of the computing system. Because activations of the first camera and the second camera are independent, functions of each of the first camera and second camera can be started, stopped, paused, unpaused, or modified individually.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not, therefore, to be considered to be limiting in scope, embodiments will be described and explained with additional specificity and details through the use of the accompanying drawings in which:

FIG. 1A illustrates a front view of an example of a mobile computing device having a first camera and a second camera;

FIG. 1B illustrates a back view of an example of a mobile computing device having a first camera and a second camera;

FIGS. 3A-3H illustrate various examples of arrangements of two or more visualizations on a display of a mobile computing device, one of the two or more visualizations corresponding to a view of a first camera, and another one of the two or more visualizations corresponding to a view of a second camera;

FIG. 7 illustrates a flowchart of an example method for calibrating a color balance of a camera; and FIG. 8 illustrates a flowchart of an example method for taking pictures or videos of a patient during different healthcare interactions and comparing the pictures or videos to determine a progress of a condition of the patient.

DETAILED DESCRIPTION

Figure 1C:
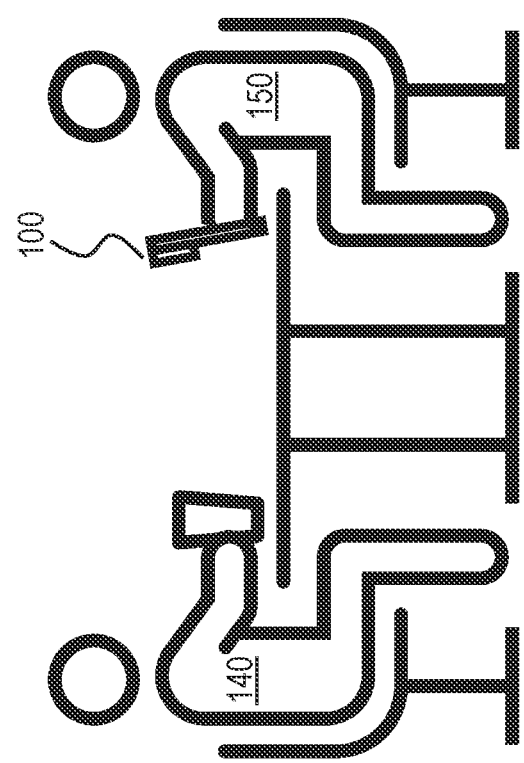
FIG. 1C illustrates an example environment in which the principles described herein may be implemented.

The embodiments described herein are related to a computing system, a method, and/or a computer program product for performing a two-way camera operation. The computing system a first camera, a second camera, a microphone, a display, one or more processors, and one or more computer-readable storage device having stored thereon executable instructions that, when executed by the one or more processors configure the computer system to perform the two-way camera operation.

FIGS. 1A and 1B illustrate a front view and a side view of an example of a mobile computing device 100, including a first camera 110 and a second camera 120. In some embodiments, the first camera 110 is a front camera, and the second camera 120 is a back camera. Existing mobile device applications generally do not allow a user to activate both of the front and back cameras 110, 120 simultaneously. For example, when the user uses a selfie mode, the front camera is activated; when the user uses a regular photo mode, the back camera is activated.

The principles described herein disclose embodiments of activating both the first camera 110 and the second camera 120 in various applications independently. It is advantageous to activate both the cameras 110, 120 independently because independent operations allow functions of each camera to be performed individually.

The independent activation of the first camera 110 and the second camera 120 can be implemented in many use cases, such as important in-person meetings. Many important in-person meetings require record-keeping or audio recording. However, audio recordings often cannot capture parties' body language or facial expressions. It is beneficial to be able to record videos of both parties during the meeting. For example, during a notary session, if a video recording is performed to capture both the notary and the person being notarized, additional security could be offered. As another example, during a healthcare interaction, such as, for example, a consultation session, a healthcare provider often discusses the risk and benefits of a treatment, and the patient needs to understand the risk and consent to the treatment. If a video recording is performed to capture both the healthcare provider's and the patient's actions and reactions, there would be less dispute when the treatment turns out to be ineffective.

A healthcare provider may include, but is not limited to, any person or entity that provides healthcare or treatment to a patient, is involved in the healthcare or treatment of a patient, and/or is involved with the billing or payment of the healthcare or treatment of a patient. A patient may include, but is not limited to, any person that is a recipient of healthcare or treatment from a healthcare provider or the recipient's family, friends, guardians, caregivers, etc. Examples of healthcare interactions may include, but are not limited to, healthcare provider-healthcare provider interactions (e.g., a discussion between two doctors about a patient's condition or care, a discussion between a dentist and a dental hygienist about a patient's dental plan, a discussion between a medical billing specialist and a medical insurance provider, etc.) and healthcare provider-patient interactions (e.g., a discussion between a physician and a patients about the patient's condition or care, a discussion between a surgeon and the legal guardian of a patient about the patient's upcoming surgery, etc.)

The principles described herein solve the above-described problem, allowing users to use a mobile device to capture two-way videos in important in-person meetings. FIG. 1C illustrates an example environment, in which two parties 140 and 150 are having an important meeting. The meeting may occur at any location, such as an office, a coffee shop, or any other convenient location. The party 150 in the meeting decides to use their mobile device 100 (corresponding to the mobile device 100 of FIGS. 1A and 1B) to take a two-way video, recording both parties' actions and communications during the meeting.

Figure 2:
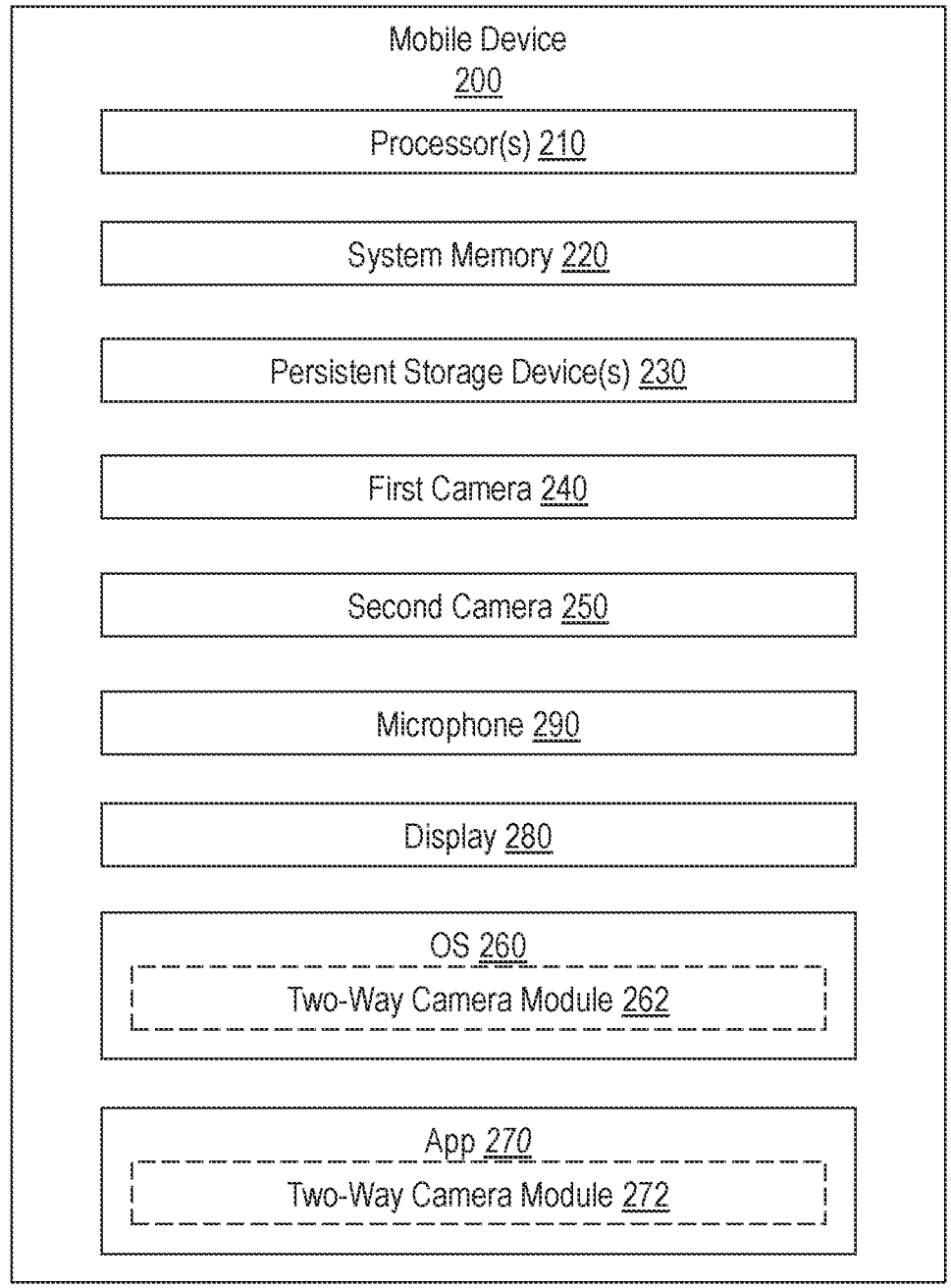
FIG. 2 illustrates an example of an architecture of a mobile computing device in which principles described herein may be employed.

Since the principles described herein are related to mobile devices, a brief description of an example architecture of a mobile device is provided with respect to FIG. 2. FIG. 2 illustrates an example of an architecture of a mobile device 200 in which the principles described herein may be implemented. The mobile device 200 includes one or more processors 210, a system memory 220, and one or more persistent storage devices 230. The mobile device 200 also includes a first camera 240, a second camera 250, a microphone 290, and a display 280. Further, the mobile device 200 has a two-way camera module 262 and/or 272, which can be implemented at the operating system 260 (OS) level (e.g., the two-way camera module 262) or at an application 270 level (e.g., the two-way camera module 272). When the two-way camera module 262 is implemented at the operating system level, many applications may be able to perform a two-way camera operation. When the two-way camera module 262 is implemented at the application level, only the particular application that implements the two-way camera module 272 is able to activate the two-way camera operation. In some embodiments, when the two-way camera operation is activated, the microphone 290 is also activated.

In some embodiments, the mobile device 200 is also configured to record a two-way video with or without audio. In some embodiments, the mobile device is configured to record a first video generated by the first camera 240 and a second video generated by the second camera 250 simultaneously. The first video and the second video are stored relationally in the one or more persistent storage devices 230. In some embodiments, an audio recording is also started when the first video and the second video are being recorded, and the recorded audio is also stored with the first video and the second video relationally in the one or more persistent storage devices 230. In some embodiments, an audio recording of the first video and/or the second video can be started, stopped, paused, unpaused, or modified individually.

Once a two-way camera operation is activated, fields of view of both cameras are received by the mobile device 200. The two fields of view are displayed simultaneously at the display 280. Many different arrangements of the two fields of view may be implemented by a developer of an application or based on user input. FIGS. 3A-3H illustrate examples of graphic user interfaces in which two fields of view received from two different cameras are simultaneously displayed on the display of a mobile device, which may correspond to the mobile device 100 of FIGS. 1A and 1B and mobile device 200 of FIG. 2.

Figure 3A:
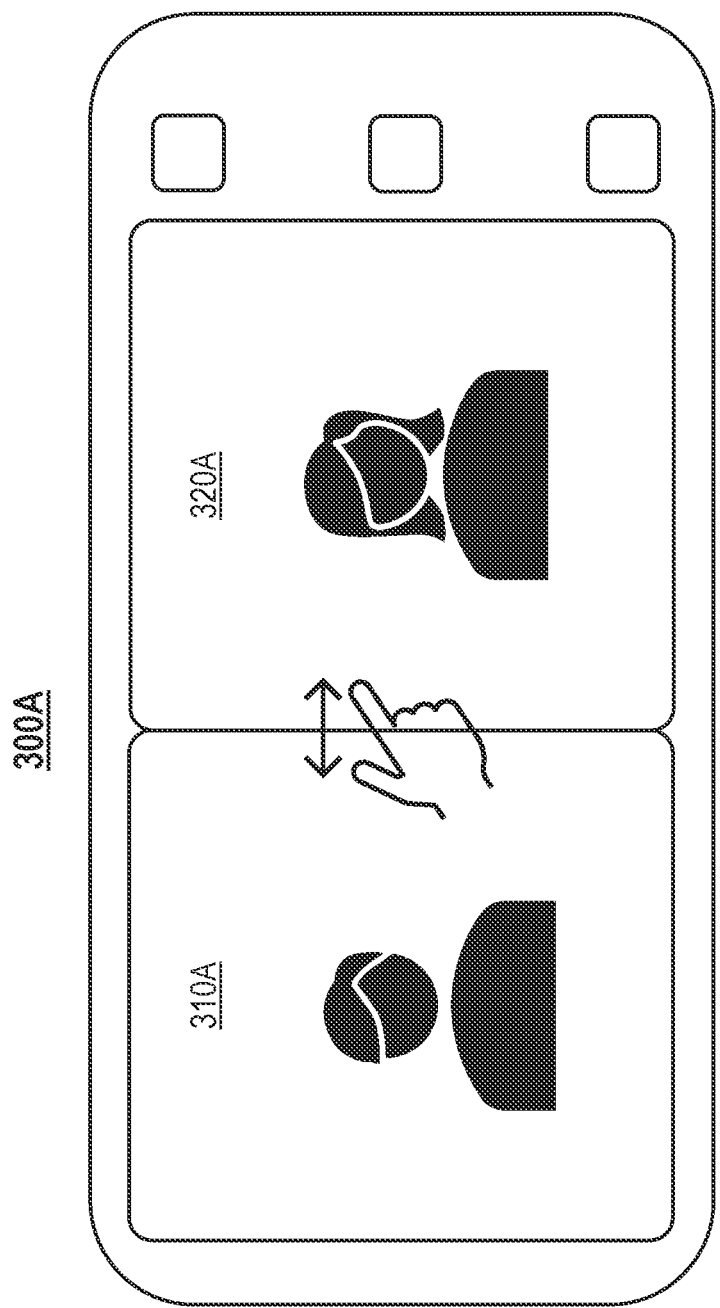

FIG. 3A illustrates an example of a user interface 300A, in which a first visualization 310A corresponding to a first camera, and a second visualization 320A corresponding to a second camera are simultaneously displayed in a split-view manner, in which the first visualization 310A and the second visualization 310B are displayed side by side and cover a whole area of the display substantially. In some embodiments, the first visualization 310A and a second visualization 320A are equal-sized and split in the middle of the display. In some embodiments, a user can interact with the split line between the two visualizations 310A, 320A to change the ratio of the two visualizations.

Figure 3B:
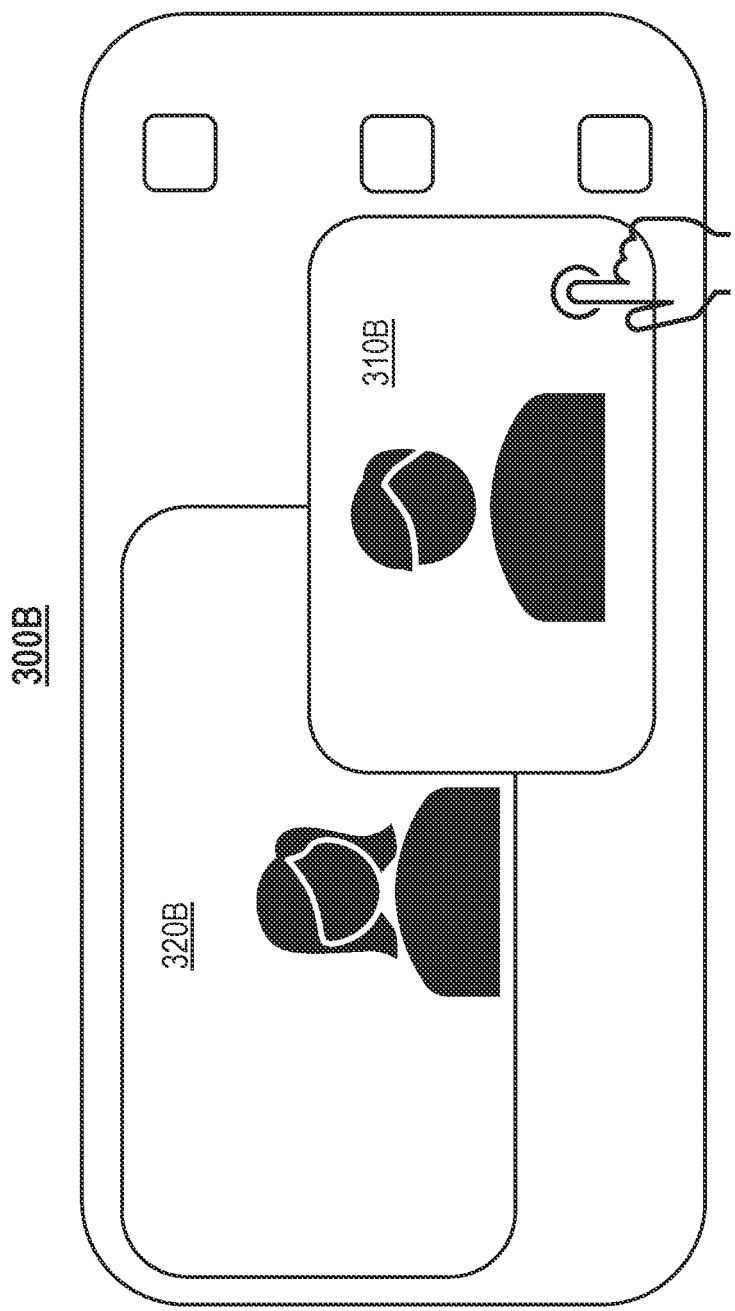

FIGS. 3B-3C illustrate additional examples of user interfaces 300B-300C, in which each of the visualizations 310B, 310C, 320B, 320C is a floating window that appears on top of another visualization or a background. Further, the floating window can be freely moved and or resized based on user input. When the display is a touch screen, a user can change the size and/or location of the visualizations 310B, 310C, 320B, 320C using hold and drag. The user can also switch the visualizations to the front or back by simply tapping the visualization. As illustrated in FIG. 3B, the first visualization 310B generated by the first camera is in the front; and as illustrated in FIG. 3C, the second visualization 320C generated by the second camera is in the front. In some embodiments, when the two visualizations overlap partially, the visualization in the front (also referred to as the front visualization) completely blocks the visualization behind the front visualization (also referred to as the back visualization). In some embodiments, the front visualization might be configured to be partially opaque, such that the back visualization can be partially seen by the user.

Figure 3D:
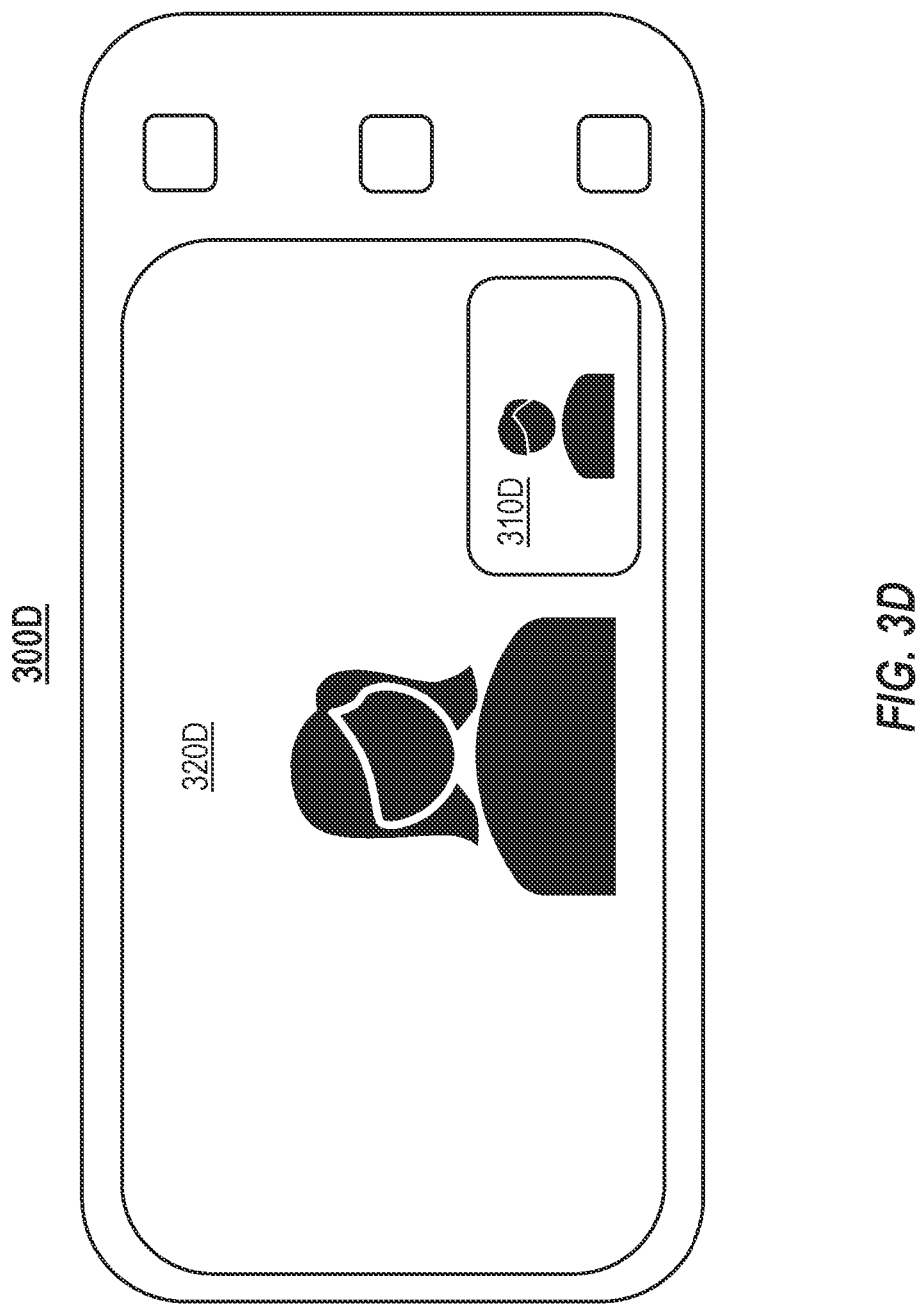
Figure 3E:
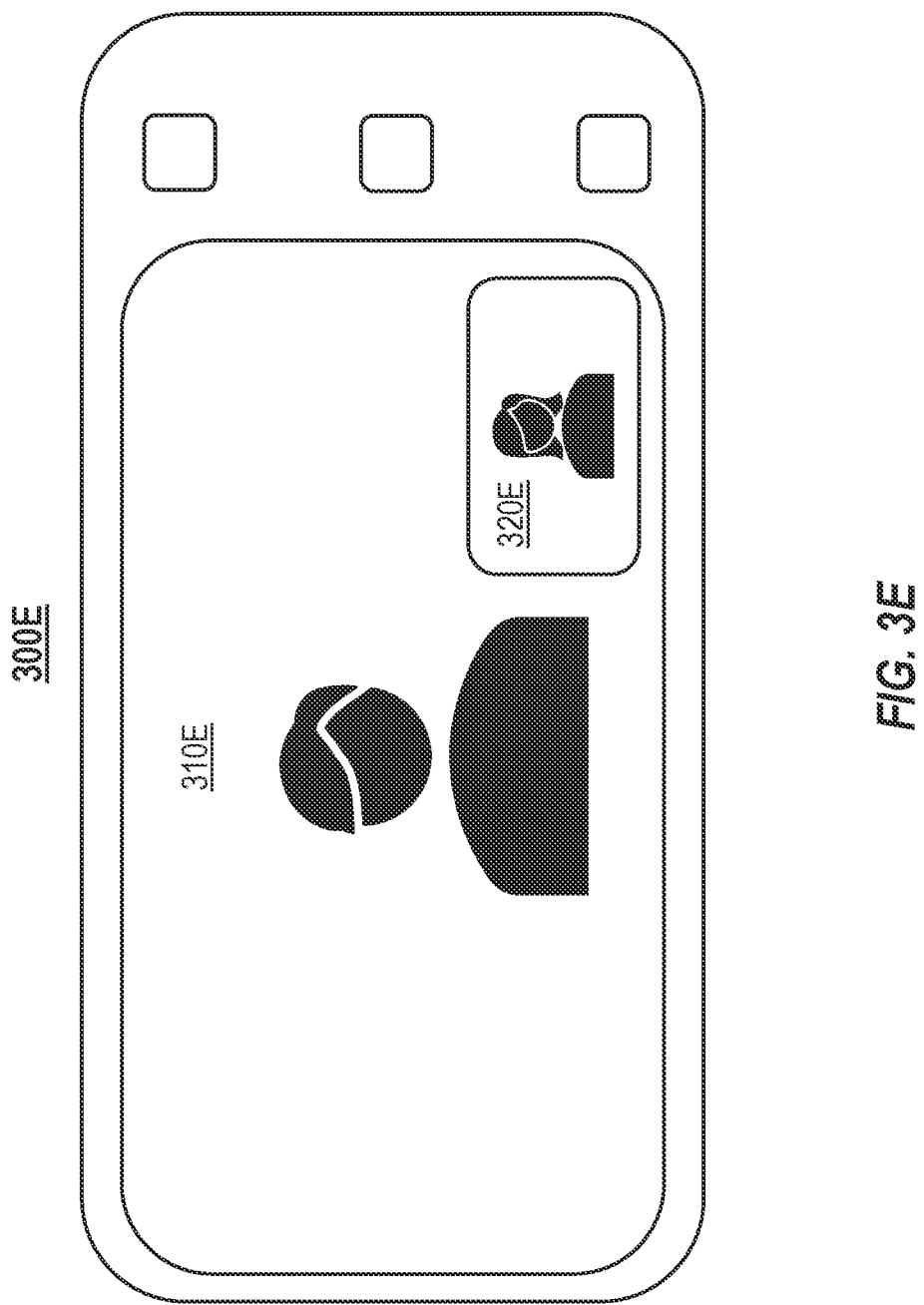

FIGS. 3D and 3E illustrate additional examples of user interfaces 300D, 300E, in which one of the visualizations takes the full screen, and the other visualization takes a fairly small portion (e.g., less than a half, or less than a quarter) of the display. In some embodiments, a user can choose which visualization to be displayed on the full screen. As illustrated in FIG. 3D, the second visualization 320D associated with the second camera is displayed on the full screen, while the first visualization 310D associated with the first camera is displayed as a floating window; as illustrated in FIG. 3E, the first visualization 310E associated with the first camera is displayed on the full screen, while the second visualization 320E associated with the second camera is displayed as a floating window.

The user interfaces illustrated in FIGS. 3A-3E may be implemented in a two-way camera video recording application, in which both parties' reactions can be recorded. For example, in a healthcare interaction, such as a healthcare provider-patient visit, the healthcare provider often explains the details about the diagnosis, prognosis, treatment plans, etc., and the patient is required to sign a consent agreement. With the video recording, the visit is better documented and the patient can refer back to and/or share with others the details about the diagnosis, prognosis, treatment plans, etc. In addition, the signed consent agreement is better documented, because based on the video, one could easily tell whether the patient understands the risk or not. As another example, in a notary situation, a signing person and a notary often sit at two opposite sides of a table. If a video could capture the signing event, the notary process would be more secure.

Figure 3G:
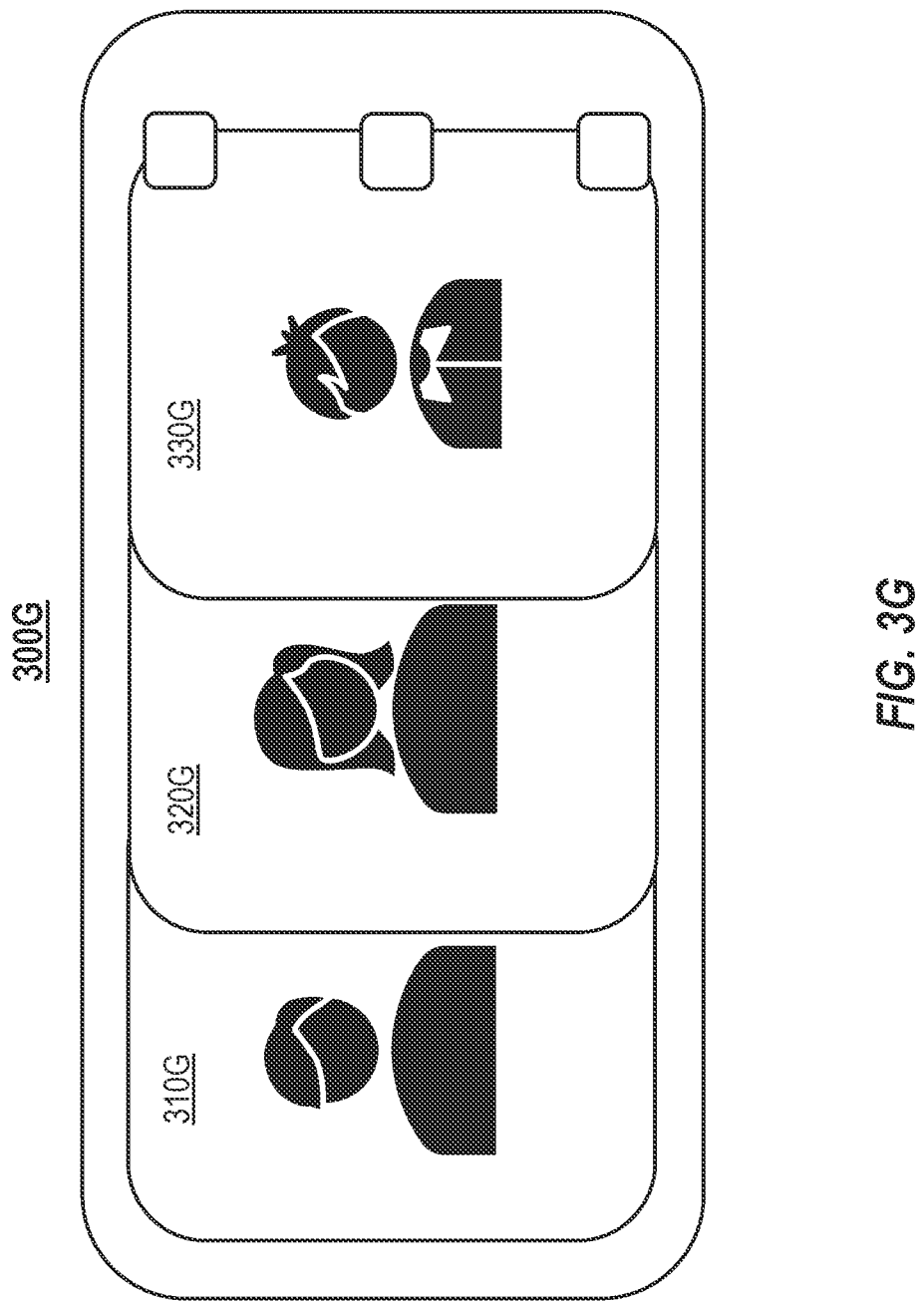
Figure 3H:
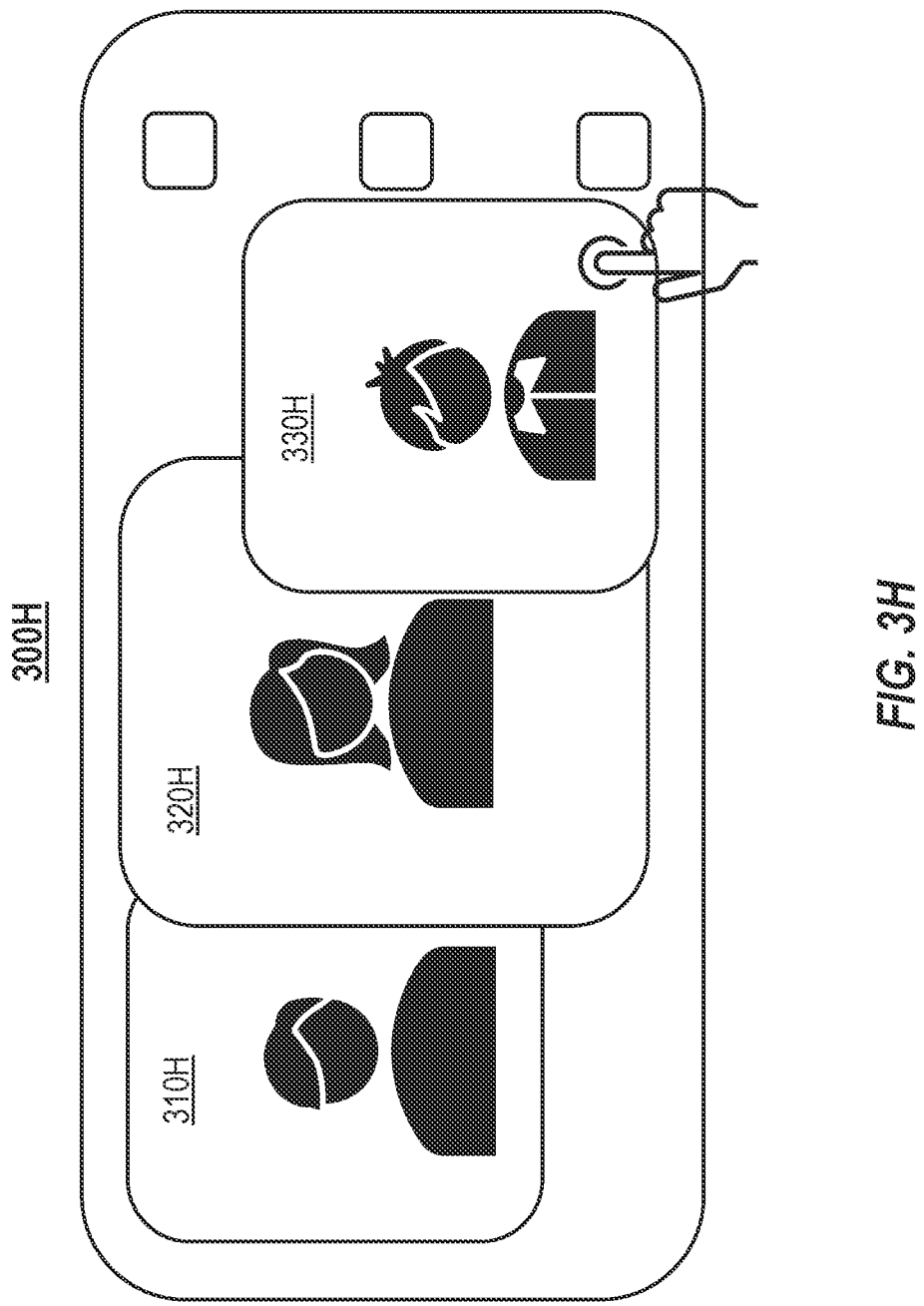

FIGS. 3F-3H further illustrate additional examples of user interfaces 300F-300H, in which not only visualizations associated with the first cameras are shown on the display, a third visualization receiving a video from a remote party is also displayed. FIG. 3F illustrates a user interface 300F, in which three visualizations 310F, 320F, and 330F are displayed in a split-view manner, taking up equal spaces. FIG. 3G illustrates another user interface 300G, in which three visualizations 310G, 320G, and 330G are displayed as partially over overlapping windows. FIG. 3H illustrates another user interface 300H, in which three visualizations 310H, 320H, and 330H are displayed as floating windows.

In some embodiments, users can use touch input or other input devices/methods to manipulate the position, the arrangement, and the size of each visualization. In some embodiments, users can also use touch input or other input methods to adjust each camera's settings individually, such as (but not limited to) focusing area, zoom, aperture, ISO, and/or shutter speed, etc.

In some embodiments, each camera of a computing system (e.g., but not limited to a mobile device) corresponds to a data stream. The data stream is fed to an application configured to have a plurality of data channels. Each of the plurality of data channels is configured to receive one of the plurality of streams of data independently. A user may be allowed to interact with the computing system to determine which data stream is fed to which data channel.

In some embodiments, the data streams may be generated by any device (which may be internal or external to the computing system). In some embodiments, there may be more than two cameras connected to the computing system. For example, in addition to a front camera and a back camera, one or more external camera may also be connected to the computing system. Such an external camera may be a component of a medical device, a security camera nearby, and/or any other type of camera implemented for any other purposes.

In some embodiments, the data streams may be stored in a storage (which may be internal or external to the computing system). In some embodiments, the storage may be a cloud storage.

In some embodiments, the data stream is also not limited to a video stream. For example, in some embodiments, the data stream may be a still image stored in a cloud storage. As another example, in some embodiments, the data stream may be a document stored in the computing system or in a cloud storage. In some embodiments, the data stream may be an audio data stream. For example, in some embodiments, the audio data stream may be generated by a microphone of the mobile device. As another example, in some embodiments, the audio data stream may be generated by an external microphone connected to the computing system.

In some embodiments, the plurality of data channels are not limited to receiving data streams from wired devices. In some embodiments, the plurality of data channels are also configured to receive data wirelessly or via a network. In some embodiments, the plurality of data channels may be configured to receive data via a wireless device via Bluetooth low energy (BLE) network, local area network (LAN), and/or Wi-Fi. In some embodiments, the plurality of data channels may be configured to receive data via a global network, such as (but not limited to) 3G, 4G, 5G networks.

In some embodiments, the two-way camera operations may be implemented in other applications, such as (but not limited to) a video call application, an asynchronous communication application, a conference call application, a healthcare application, and/or an electronic signature application. For example, the existing conference call application only allows one camera (often the front camera) to be activated. The principles described herein allow a conference call application, an asynchronous communication application, or video call application to activate and display fields of view received from both cameras.

In some embodiments, the principles described herein are implemented in a healthcare application configured to allow a healthcare provider to take two-way videos during a healthcare interaction. The healthcare application is configured to record a first video dataset, a second video dataset, and an audio dataset during a healthcare interaction. The audio dataset contains a conversation between a healthcare provider and a patient during the healthcare interaction. The first video dataset contains actions of the healthcare provider during the healthcare interaction, and the second video dataset contains actions of the patient during the healthcare interaction. The health application is also configured to store the first video dataset, the second video dataset, and the audio dataset as an artifact associated with a case of the patient.

In some embodiments, the healthcare application is configured to retrieve any one of the first video dataset, the second video dataset, or the audio dataset and replay the retrieved dataset individually. In some embodiments, the healthcare application is configured to retrieve one of the first video dataset or the second video dataset and the audio dataset and replay the retrieved video dataset and the audio dataset simultaneously. In some embodiments, the healthcare application is configured to retrieve the first video dataset, the second video dataset, and the audio dataset, and replay all of them in a same user interface.

In some embodiments, the healthcare application is also configured to allow a healthcare provider to take a picture of a patient. Many medical conditions are associated with the color of a patient's skin, the color of the patient's eyes, and/or the color of the patient's other body parts. It is advantageous to allow a healthcare provider to take pictures and/or videos of the patient's condition and compare different pictures and/or videos taken at different times to determine whether the patient's condition is improving or worsening. However, different cameras take slightly different colored pictures and/or videos, and different ambient environments also have different lighting conditions. Even the same room on different days may have different lighting conditions depending on the weather.

The principles described herein solve the above-described problem by calibrating a camera based on a reference color chart or based on colors from pictures and/or videos taken by another camera. The reference color chart may be a printed color chart containing a set of different colored patches, and these colors have been preset as the standard colors. In some embodiments, calibrating the camera includes causing the camera to take a picture of the reference color chart, and comparing a set of colors in the picture with a correct set of colors corresponding to the set of standard colors printed on the reference color chart to determine whether the set of colors in the picture matches the correct set of colors. In response to determining that the set of colors does not match the correct set of colors, the color balance of the camera is adjusted. The adjustment causes the camera to take pictures and/or videos with the correct set of colors.

In some embodiments, a different reference color chart is used for taking pictures and/or videos of different health conditions. For example, a first reference color chart is used to calibrate a camera for taking a picture and/or a video of a patient's skin, and a second reference color chart is used to calibrate a camera for taking a picture and/or a video of a patient's eye.

In some embodiments, a first camera may have a set of colors that may be different from a set of colors of a second camera. For example, a first camera may have different color presets from the color presets of a second camera. As another example, a user of a first camera may adjust the color settings of the first camera such that a set of colors of the first camera are different from a set of colors of a second camera. In some embodiments, the first camera may be calibrated such that the colors of the first camera match the standard colors of a second camera. In some embodiments, calibrating a first camera to a second camera includes causing the first camera to take a first picture of a person, place, or thing; causing the second camera to take a second picture of the person, place, or thing; comparing a first set of colors in the first picture with a second set of colors in the second picture to determine whether the first set of colors matches the second set of colors. In response to determining that the set first of colors does not match the second set of colors, the color balance of the first camera is adjusted. The adjustment causes the first camera to take pictures and/or videos with the second set of colors.

Figure 4:
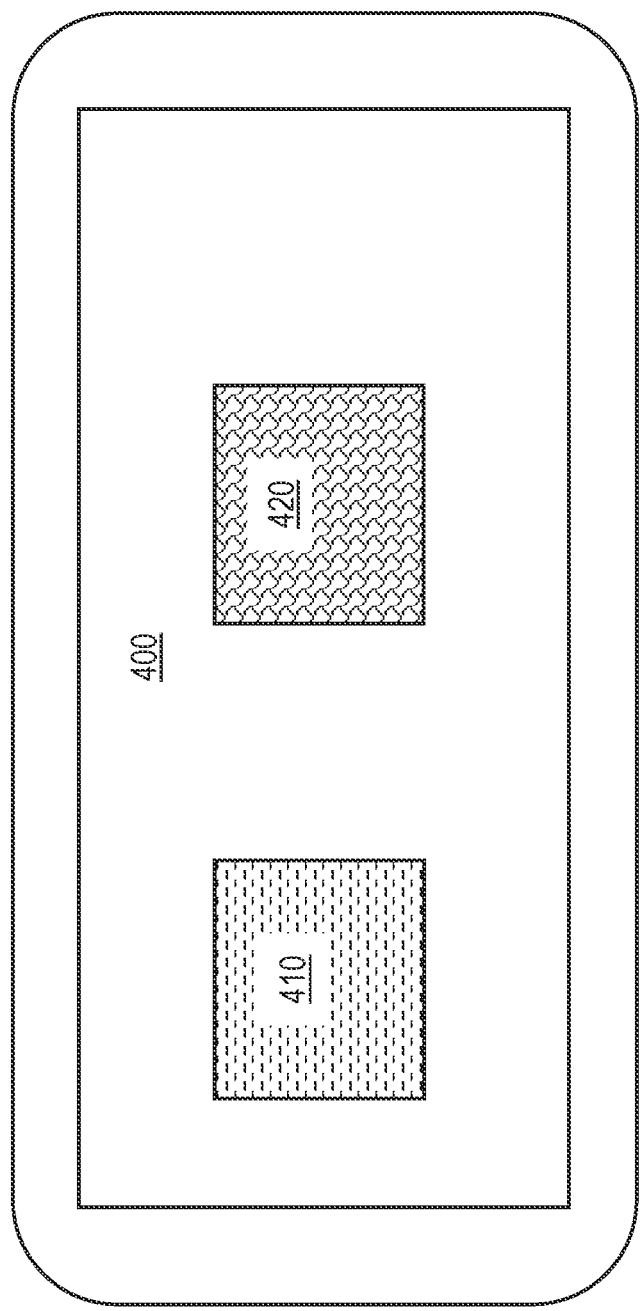
FIG. 4 illustrates an example embodiment of calibrating a color balance of a front camera or a back camera.

FIG. 4 illustrates an example user interface 400 of a mobile device for calibrating a camera of the mobile device. The camera is configured to take a picture 410 of a reference color chart and compare the picture 410 of the reference color chart with a reference picture 420, including a set of correct colors. In some embodiments, the reference picture 420 is stored with the mobile device. In some embodiments, the reference picture 420 is stored in a server that provides the healthcare application. If each color in the picture 410 taken by the camera is sufficiently close to each color in the reference picture 420, the healthcare application determines that the color balance of the camera is good. If at least one color in the picture 410 taken by the camera is sufficiently different from at least one color in the reference picture 420, the healthcare application adjusts the color balance of the camera.

After the camera of the mobile device is calibrated, the mobile device can then be used to take pictures and/or videos of patient's conditions. In some embodiments, the healthcare application is also configured to store the picture of the patient's condition as an artifact associated with a case of the patient.

In some embodiments, the healthcare application is also configured to compare a picture of a patient's condition with another set of reference colors to automatically perform a diagnosis. For example, if a color of a patient's eye matches a reference color, the health application determines that the patient likely has jaundice.

In some embodiments, the picture is timestamped, and the healthcare application is also configured to compare pictures and/or videos taken at different times to determine whether the patient's condition has been improved or worsened. Note, the different pictures and/or videos of the same patient may be taken by the same mobile device or different mobile devices in the same lighting environment or different lighting environments. Since each camera has been calibrated based on the same color reference chart, the same color in different lighting environments taken by different devices should correspond to the same color in the pictures and/or videos. Thus, when two pictures and/or videos show different colors, the color change indicates that the condition of the patient likely has changed.

Additionally, there are numerous medical devices in a healthcare provider's facility. These medical devices often have their own monitors. The data generated by these medical devices are displayed on their corresponding monitors. Even though a healthcare provider can see the data displayed on these monitors, the healthcare provider may or may not have easy access to such data. It is advantageous to allow the healthcare provider to take a picture of the monitor and store the picture as an artifact associated with a case of the patient. However, different monitors have different refresh rates, and different mobile devices also have different frame rates. When the refresh rates and the frame rate mismatch, the picture of the monitor taken by the mobile device would include one or more trippy lines that go all over the screen.

The principles described herein solve the above-described problem by causing a camera of a mobile device to take a sequence of pictures and/or videos of a monitor and identify a refresh rate based on the sequence of pictures and/or videos. The frame rate of the camera is then adjusted based on the refresh rate. In some embodiments, the frame rate is adjusted to be the same as the refresh rate. In some embodiments, the frame rate is adjusted to be a half or a third of the refresh rate. In some embodiments, the frame rate is adjusted to be twice or three times the refresh rate.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 5:
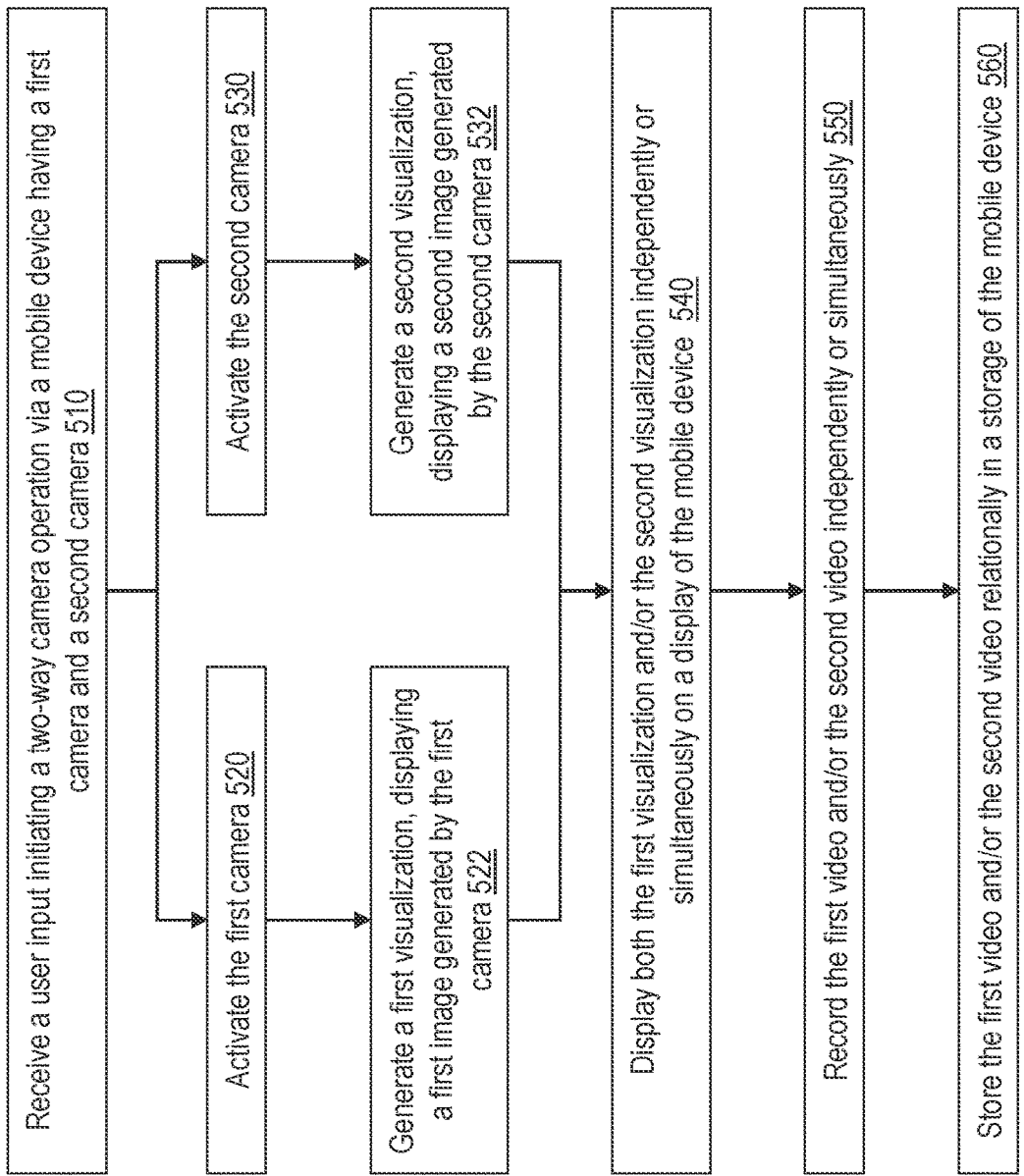
FIG. 5 illustrates a flowchart of an example method for performing a two-way camera operation.

FIG. 5 illustrates a flowchart of an example method 500 for performing a two-way camera operation independently. The method 500 includes receiving a user input initiating a two-way camera operation via a mobile device having a first camera and a second camera (act 510). The method 500 further includes activating the first camera (act 520) and generating a first visualization to display a first image generated by the first camera (act 522). The method 500 further includes activating the second camera (act 530) and generating a second visualization, displaying a second image generated by the second camera (act 532). The activation of the first camera and second camera (acts 520, 530) can be performed simultaneously or sequentially. The generation of the first visualization and the second visualization (act 522, 532) can also be performed simultaneously or sequentially.

The method 500 further includes displaying both the first visualization and the second visualization simultaneously on a display of the mobile device (act 540). In some embodiments, the method 500 further includes recording the first video and/or the second video independently and/or simultaneously (act 550) and storing the first video and/or the second video relationally in a storage of the mobile device (act 560). In some embodiments, a timing of the first video and the second video are synchronized. In some embodiments, a user is allowed to replay the first video or the second video separately, or replay both of them simultaneously in various views, as shown in FIGS. 3A-3H.

In some embodiments, the method 500 also includes activating a microphone of the mobile device when the first camera or the second camera is activated (act 520 or 530) and recording audio data generated by the microphone simultaneously when the first video and/or the second video are recorded. In some embodiments, the recorded audio is also stored relationally with the first video and/or the second video. Because activations of the first camera and the second camera are independent, functions of each of the first camera and second camera can be started, stopped, paused, unpaused, or modified individually. For example, in some embodiments, a recording of the first camera may be paused while a recording of the second camera continues unpaused. As another example, in some embodiments, the user may pause a recording of a first data stream (e.g., the first camera) fed to a first data channel, may interact with the computing system to change to the input of the first data channel from the first data stream to a second data stream (e.g., the second camera) while the recording is paused, and may unpause the recording such that the second data stream is then recorded.

After the first video, the second video, and the audio are recorded, they can be replayed individually or in any combination. For example, a user can interact with the mobile device or a mobile app to play the first video, the second video, or the audio individually. The user can also interact with the mobile device or the mobile app to play the first video with the audio together as a first audiovisual file. Alternatively, the user can also play the second video with the audio together as a second audiovisual file. Alternatively, the user can also play the first video and/or the second video simultaneously in a single user interface with or without the audio.

Figure 6:
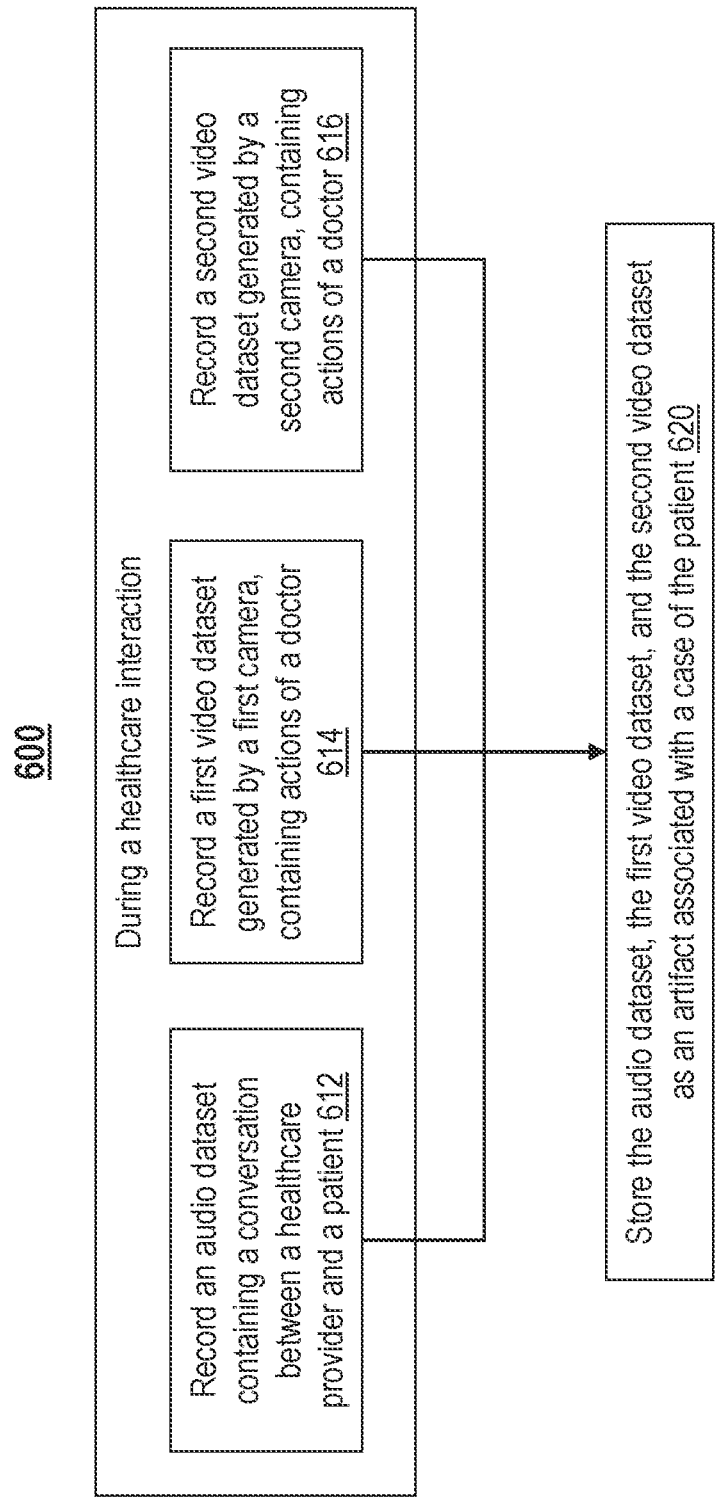
FIG. 6 illustrates a flowchart of an example method for recording a healthcare interaction.

In some embodiments, the method 500 is implemented in a healthcare application (e.g., a mobile application) that allows a user (e.g., a patient or a healthcare provider) to record a healthcare consultation session. FIG. 6 illustrates a flowchart of an example method 600 for recording a healthcare provider-patient consultation session. The method 600 includes recording an audio dataset containing a conversation between a healthcare provider during the healthcare provider-patient consultation session (act 612). The method 600 further includes recording a first video dataset generated by a first camera (act 614). The first video dataset contains actions of a healthcare provider during the healthcare provider-patient consultation session. The method 600 further includes recording a second video dataset generated by a second camera (act 616). The second video dataset contains actions of a patient during the healthcare provider-patient consultation session. The method 600 further includes storing the audio dataset, the first video dataset, and the second video dataset as an artifact associated with a case of the patient (act 620). The recorded first video dataset, second video dataset, and audio dataset can then be replayed individually or in any combination by the health care provider and/or the patient.

In some embodiments, the health application is also configured to allow a healthcare provider to take pictures and/or videos of a patient. The pictures and/or videos are associated with a condition of the patient. In some cases, the condition is associated with a color of the patient's skin, a color of the patient's eyes, and/or a color of the patient's other body parts. However, different cameras often take pictures and/or videos with slightly different colors, and different environments have different lighting conditions. The factors related to the camera and the environment can affect the colors of the pictures and/or videos taken. The principles described herein solve this problem by a method of calibrating a camera based on a reference color chart.

FIG. 7 illustrates a flowchart of an example method 700 for calibrating a camera based on a reference color chart. The method 700 may be performed by a mobile device or a healthcare application of the mobile device. The method 700 includes taking a picture and/or a video of a reference color chart by a camera of a device (act 710). The reference color chart has a set of standard colors (or patches of colors) printed thereon. The method 700 further includes comparing a set of colors in the picture (taken by the camera) with a correct set of colors corresponding to the set of standard colors printed on the reference color chart (act 720) to determine whether the set of colors in the picture matches the correct set of colors. In response to determining that at least one color in the picture (taken by the camera) does not match at least one color in the correct set of colors, a color balance of the camera is adjusted, causing the camera to take pictures and/or videos with the correct set of colors (act 730).

After the camera of the mobile device is calibrated, the pictures and/or videos taken by the camera can then be used to perform a diagnosis. In some embodiment, the method 700 further includes taking a picture and/or a video of a patient after the calibration and comparing a color in the picture with a reference color associated with a condition to determine whether the patient has the condition. In some embodiments, the health application is also configured to compare multiple pictures and/or videos of the same patient taken at different times to determine whether the patient's condition has been improved.

FIG. 8 illustrates a flowchart of an example method 800 for taking pictures and/or videos of a patient at different times and comparing the pictures and/or videos to determine a progress of a condition of the patient. The method 800 includes taking a first picture of a patient by a camera of a mobile device after a first calibration during a first healthcare provider-patient consultation session (act 810). The first calibration corresponds to the method 700 in FIG. 7. The method 800 further includes storing the first picture as a first artifact associated with a case of the patient (act 820). The method 800 further includes taking a second picture of a patient by a camera of a mobile device after a second calibration during a second healthcare provider-patient consultation session (act 830). The second calibration also corresponds to the method 700 in FIG. 7. The method 800 further includes storing the second picture as a second artifact associated with the case of the patient (act 840).

The method 800 further includes comparing the first picture with the second picture to determine whether a condition of the patient has been improved or worsened (act 850). The determination can then be stored as a contextual dataset with the case of the patient (act 860). In some embodiments, the contextual dataset may be stored as a label of the first picture or the second picture. Note, the first picture and the second picture may or may not be taken by a same camera, a same environment, and/or a same lighting condition. Because the first picture and the second picture are taken after the same calibration process, even though the first picture and the second picture may be taken by different mobile devices and/or in different lighting conditions, the same color shown on both pictures and/or videos should reflect the same condition of the patient.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may comprise or utilize a special-purpose or general-purpose computer system that comprises computer hardware, such as, for example, one or more processors and system memory, as discussed in greater detail below. Configurations within the scope of the present invention also comprise physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, configurations of the invention can comprise at least two distinctly different kinds of computer-readable media: computer storage media and transmission media.

Computer storage media are physical storage media that store computer-executable instructions and/or data structures. Physical storage media comprise computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can comprise a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be comprised within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be comprised in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may comprise a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Some configurations, such as a cloud-computing environment, may comprise a system that comprises one or more hosts that are each capable of running one or more virtual machines. During operation, virtual machines emulate an operational computing system, supporting an operating system and perhaps one or more other applications as well. In some configurations, each host comprises a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

For the processes and methods disclosed herein, the operations performed in the processes and methods may be implemented in differing order. Furthermore, the outlined operations are only provided as examples, and some of the operations may be optional, combined into fewer steps and operations, supplemented with further operations, or expanded into additional operations without detracting from the essence of the disclosed embodiments.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computing system comprising:
a first camera;
a second camera;
a microphone;
a display;
one or more processors; and
one or more computer-readable hardware storage devices having stored thereon computer-executable instructions that are structured such that, when executed by the one or more processors, configure the computing system to perform independently at least:
receive a user input initiating a two-way camera operation using both the first camera and the second camera;
activate the first camera and generate a first visualization, displaying a first image generated by the first camera;
activate the second camera and generate a second visualization, displaying a second image generated by the second camera;
display both the first visualization and the second visualization simultaneously on the display of the computing system;
calibrate a color balance of the first camera or the second camera based on a reference color chart having a set of standard colors printed thereon, wherein calibrating the color balance of the first camera or the second camera includes:
taking a picture or a video of the reference color chart by the first camera or the second camera,
comparing a set of colors in the picture with a correct set of colors corresponding to the set of standard colors printed on the reference color chart to determine whether the set of colors in the picture matches the correct set of colors, and
in response to determining that the set of colors does not match the correct set of colors, adjusting the color balance of the first camera or the second camera, causing the first camera or the second camera to take pictures or videos with the correct set of colors; and
wherein because activations of the first camera and the second camera are independent, functions of each of the first camera and second camera can be started, stopped, paused, unpaused, or modified individually.

2. The computing system of claim 1, the computing system further configured to:
receive a second user input, indicating starting a video recording;
in response to the second user input, record a first video generated by the first camera or a second video generated by the second camera simultaneously; and
store the first video or the second video relationally in the one or more computer-readable hardware storage devices.

3. The computing system of claim 2, the computing system further configured to:
activate the microphone when the first camera or the second camera is activated;
start an audio recording when the first video and the second video are simultaneously recorded; and
store the recorded audio with the first video and the second video relationally in the one or more computer-readable hardware storage devices.

4. The computing system of claim 1, wherein:
the computing system is configured to have a plurality of data channels, each configured to receive a data stream;
any one of the plurality of data channels is configured to receive a video data stream from the first camera or the second camera.

5. The computing system of claim 4, wherein the plurality of data channels are also configured to receive a data stream generated by an external device or stored in a storage, and display each data stream in one of a plurality of visualizations.

6. The computing system of claim 1, the computing system further configured to:
record a healthcare interaction as a first video dataset, a second video dataset, and an audio dataset, wherein the audio dataset contains a conversation between a healthcare provider and a patient during the healthcare interaction, the first video dataset contains actions of the healthcare provider during the healthcare interaction, the second video dataset contains actions of the patient, the first video is generated by the first camera, and the second video is generated by the second camera; and
store the first video dataset, the second video dataset, and the audio dataset as an artifact associated with a case of the patient.

7. The computing system of claim 1, the computing system further configured to:
take a first picture of a patient by the first camera or the second camera after a first calibration during a first healthcare interaction;
store the first picture as a first artifact associated with a case of the patient;
take a second picture of the patient by the first camera or the second camera after a second calibration during a second healthcare interaction;
store the second picture as a second artifact associated with the case of the patient;
compare the first picture with the second picture to determine whether a condition of the patient has been improved or worsened; and
store the determination as a contextual dataset with the case of the patient.

8. The computing system of claim 1, the computing system further configured to:
take a sequence of pictures or a video of a monitor by the first camera or the second camera;
identify a refresh rate of the monitor;
adjust a frame rate of the first camera or the second camera based on the refresh rate of the monitor; and
take a picture of the monitor based on the adjusted frame rate.

9. The computing system of claim 8, wherein the monitor is a monitor of a medical device.

10. A method implemented at a computing system for independently performing a two-way camera operation, the computing system comprising a first camera, a second camera, a microphone, a display, and a computer-readable hardware storage device, the method comprising:
receiving a user input initiating a two-way camera operation using both the first camera and the second camera;

activating the first camera and generate a first visualization, displaying a first image generated by the first camera;

activating the second camera and generate a second visualization, displaying a second image generated by the second camera;

displaying both the first visualization and the second visualization simultaneously on the display of the computing system, taking a sequence of pictures or a video of a monitor by the first camera or the second camera;

identifying a refresh rate of the monitor;

adjusting a frame rate of the first camera or the second camera based on the refresh rate of the monitor; and taking a picture or a video of the monitor based on the adjusted frame rate, wherein because activations of the first camera and the second camera are independent, functions of each of the first camera and second camera can be started, stopped, paused, unpaused, or modified individually.

11. The method of claim 10, wherein the first visualization and the second visualization are displayed in a split-view manner, in which the first visualization and the second visualization are displayed side by side and cover a whole area of the display substantially.

12. The method of claim 10, the method further comprising:

receiving a second user input, indicating starting a video recording;

in response to the second user input, simultaneously performing the following:
  recording a first video generated by the first camera,
  recording a second video generated by the second camera, and
  recording an audio generated by the microphone; and
storing the first video, the second video, and the audio relationally in the computer-readable hardware storage device.

13. The method of claim 12, the method further comprising:

recording a healthcare interaction as a first video dataset, a second video dataset, and an audio dataset, wherein the audio dataset contains a conversation between a healthcare provider and a patient during the healthcare interaction, the first video dataset contains actions of the healthcare provider during the healthcare interaction, the second video dataset contains actions of the patient, the first video is generated by the first camera, and the second video is generated by the second camera; and storing the first video dataset, the second video dataset, and the audio dataset as an artifact associated with a case of the patient.

14. The method of claim 10, the method further comprising calibrating a color balance of the first camera or the second camera based on a reference color chart having a set of standard colors printed thereon, comprising:

taking a picture or a video of the reference color chart by the first camera or the second camera;

comparing a set of colors in the picture with a correct set of colors corresponding to the set of standard colors printed on the reference color chart to determine whether the set of colors in the picture matches the correct set of colors; and in response to determining that the set of colors does not match the correct set of colors, adjusting the color balance of the first camera or the second camera, causing the first camera or the second camera to take pictures or videos with the correct set of colors.

15. The method of claim 14, the method further comprising:

taking a first picture of a patient by the first camera or the second camera after a first calibration during a first healthcare interaction;

storing the first picture as a first artifact associated with a case of the patient;

taking a second picture of the patient by the first camera or the second camera after a second calibration during a second healthcare interaction;

storing the second picture as a second artifact associated with the case of the patient;

comparing the first picture with the second picture to determine whether a condition of the patient has been improved or worsened; and storing the determination as a contextual dataset with the case of the patient.

16. The method of claim 10, wherein the monitor is a monitor of a medical device.

17. A computer program product comprising one or more hardware storage devices having stored thereon computer-executable instructions that are structured such that, when the computer-executable instructions are executed by one or more processors of a computing system, the computing system comprising a first camera, a second camera, a microphone, and a display, the computer-executable instructions cause the computing system to perform independently at least:

receive a user input initiating a two-way camera operation using both the first camera and the second camera;

activate the first camera and generate a first visualization, displaying a first image generated by the first camera;

activate the second camera and generate a second visualization, displaying a second image generated by the second camera;

display both the first visualization and the second visualization simultaneously on the display of the computing system;

receiving a second user input, indicating starting a video recording;

in response to the second user input, simultaneously performing the following:
  recording a first video generated by the first camera,
  recording a second video generated by the second camera, and
  recording an audio generated by the microphone;
storing the first video, the second video, and the audio relationally in the one or more hardware storage device, take a sequence of pictures or a video of a monitor by the first camera or the second camera;

identify a refresh rate of the monitor;

adjust a frame rate of the first camera or the second camera based on the refresh rate of the monitor; and take a picture or a video of the monitor based on the adjusted frame rate, wherein because activations of the first camera and the second camera are independent, functions of each of the first camera and second camera can be started, stopped, paused, unpaused, or modified individually.

* * * * *